United States Patent [19]

Jaen et al.

[11] Patent Number: 5,342,942
[45] Date of Patent: Aug. 30, 1994

[54] PYRAZOLOQUINAZOLONE DERIVATIVES AS NEUROTROPHIC AGENTS

[75] Inventors: Juan C. Jaen, Plymouth; Bradley W. Caprathe, Redford, both of Mich.

[73] Assignee: Warner-Lambert Company, Ann Arbor, Mich.

[21] Appl. No.: 38,374

[22] Filed: Mar. 29, 1993

Related U.S. Application Data

[63] Continuation-in-part of Ser. No. 895,979, Jun. 9, 1992, abandoned.

[51] Int. Cl.$^5$ .............. C07D 487/04; C07D 487/14; C07D 491/147; C07D 495/14
[52] U.S. Cl. ................. 544/250; 544/247; 544/251; 544/89; 544/90; 544/91; 544/94; 540/578; 435/7.1; 435/7.21; 435/7.23; 548/251; 548/369.7
[58] Field of Search .................. 544/250; 514/267

[56] References Cited

U.S. PATENT DOCUMENTS

| | | | |
|---|---|---|---|
| 4,247,555 | 1/1981 | Sircar et al. | 514/267 |
| 4,261,996 | 4/1981 | Sircar et al. | 544/250 |
| 4,261,997 | 4/1981 | Sircar et al. | 544/250 |
| 4,510,143 | 4/1985 | Westwood et al. | 544/250 |
| 4,762,840 | 8/1988 | Rowlands et al. | 544/250 |
| 5,175,153 | 12/1992 | Bigge et al. | 546/22 |

OTHER PUBLICATIONS

Sircar et al., *J. Med. Chem.* 24, pp. 735–742 (1981).
Tachibana et al., *Chemical Abstracts*, vol. 112, No. 207749 (Abstract for JP 01210950 Aug. 24, 1989) (1990).
*Medicinal Chemistry* (2nd Ed.) by Alfred Burger, pp. 72–75 and 79–80 (1960).
J. C. Sircar, T. Capiris, S. J. Kesten, *J. Heterocycl. Chem.* 1981, (18), 117–121.

*Primary Examiner*—Emily Bernhardt
*Attorney, Agent, or Firm*—Merchant, Gould, Smith, Edell, Welter & Schmidt

[57] ABSTRACT

Pyrazolo[5,1-b]quinazoline compounds, salts thereof, methods of production, intermediates in their production, pharmaceutical compositions containing said compounds, and methods for treating neurodegenerative disorders, tumors of neuronal origin, inflammation, allergy, and pain, and methods for screening compounds that interact with the neurotrophic receptors using said compositions are disclosed.

18 Claims, 6 Drawing Sheets

PYRAZOLOQUINAZOLONE DERIVATIVES AS NEUROTROPHIC AGENTS

This application is a continuation-in-part of copending U.S. Ser. No. 895979, filed Jun, 9, 1992, now abandoned.

FIELD OF THE INVENTION

The present invention relates to novel pyrazoloquinazolone compounds and pharmaceutical compositions containing pyrazoloquinazolone compounds that are useful pharmacological agents in the diagnosis and treatment of a variety of neurological and neurodegenerative disorders, methods for production of the compounds, and methods for treating neurodegenerative disorders. The novel pyrazoloquinazolone compounds of the present invention are also useful as screening tools for the discovery of novel agents with neurotrophic or antineurotrophic activity.

BACKGROUND ART

Nerve growth factor (NGF) was first described by Levi-Montalcini (*J. Exp Zool.*, 116:321-362 (1951)) as an activity secreted by a mouse sarcoma tumor implanted into a chick embryo. Both sensory ganglion and sympathetic ganglion neurons grew neurites into the sarcoma, which also supported the growth of peripheral neurons in culture. The factor, purified to homogeneity from mouse submandibular glands in 1956 by Levi-Montalcini and Cohen (*Proc. Natl. Acad. Sci. USA*, 42:571 (1956)) consists of a complex (referred to as 7S NGF, from its sedimentation coefficient) comprised of three different subunits. NGF's neurotrophic activity resides entirely within the β-subunit (hereinafter referred to as NGF), a dimer consisting of two equivalent monomers of approximately 13,000 dalton molecular weight.

A role for NGF as a neurotrophic factor in the peripheral nervous system (PNS) was rapidly established through both in vitro and in vivo experiments (Levi-Montalcini and Angeletti, *Physiol. Rev.*, 48:534-569 (1968); Johnson, et al., *Science*, 210:916-918 (1980)). These studies demonstrated that sympathetic neurons of the PNS have an absolute requirement for NGF for survival throughout life, while many sensory neurons require NGF during certain periods of development. As an extrapolation of these early findings, NGF and related neurotrophic factors have been shown recently to be useful in the treatment of sensory and autonomic neuropathies (Kaplan, et al., *Science*, 252:554-558 (1991)). More specifically, NGF prevents the development of small-fiber sensory neuropathies that result from the use of taxol, a chemotherapeutic agent (Apfel, et al., *Ann. Neurol.*, 29:87-90 (1991)). NGF is also efficacious against the development of large-fiber sensory neuropathies resulting from the anticancer drug cisplatin, and in an animal model of diabetes-induced neuropathy (Apfel, et al., *Ann. Neurol.*, 31:76-80 (1992)).

NGF is synthesized in the periphery by the non-neuronal target tissues innervated by the NGF-dependent neurons. Upon binding of NGF to its receptor, the NGF receptor complex is internalized by the neuron and retrogradely transported back to the neuron cell body. NGF's intracellular mechanism of action is not yet fully understood.

It was not until 1983 that NGF was detected in the central nervous system (CNS) (Ayer-LeLievre, et al., *Medical Biology*, 61:296-304 (1983)). This discovery was preceded by the demonstration that the cholinergic neurons of the basal forebrain are responsive to NGF (Schwab, et al., *Brain Res.*, 168:473-483 (1979)). These neurons possess NGF receptors which are undistinguishable from the NGF receptors in the periphery. As in the PNS, NGF is synthesized by the target regions of the sensitive neurons, the hippocampus and the neocortex. NGF secreted by these target regions binds to its receptor(s) on NGF-dependent neurons, and is required for the development and survival of these neurons.

In animal models, lesions of the septo-hippocampal neuronal pathway, which connects the neurons of the basal forebrain to the hippocampus, results in the degeneration of the neurons in the medial septal nucleus, due to the lack of trophic support that is normally provided by hippocampal NGF. This neuronal degeneration can be prevented by administration of NGF into the cerebrospinal fluid (CSF) of the animals via a miniosmotic pump (Gage, et al., *J. Comp. Neurol.*, 269:147-155 (1988); Hagg, et al., *Exp. Neurol.*, 101:303-312 (1988); Kromer, et al., *Science*, 235:214-216 (1987)). NGF also enhances the ability of brain cholinergic neurons to survive a chemical insult. In animals with atrophied or lesioned basal forebrain cholinergic neurons, NGF has been shown to reverse the associated behavioral impairment (Fisher, et al., *J. Neurosci.*, 11:1889-1906 (1991); Tuszynski, et al., *Ann. Neurol.*, 30:625-636 (1991)).

Even though there is no direct evidence for a reduced level of NGF in neurodegenerative disorders such as Alzheimer's disease (AD), the sensitivity of brain cholinergic neurons to NGF treatment is specially interesting, since these neurons are consistently depleted in AD. In fact, recent clinical findings in humans support the interpretation that treatment with NGF is useful in the treatment of AD (Olson, et al., *J. Neural Transm.*, (P-D Sect) 4:79 (1992)).

NGF produces its effects by binding to receptors in the cytoplasmic membrane of NGF-sensitive neurons. Two types of NGF receptors have been identified to date. The low affinity NGF receptor (Johnson, et al., *Cell*, 47:545-554 (1986)), known as p75 because it has a molecular weight of about 75,000 dalton, binds NGF with an affinity ($K_D = 10^{-9}$M) several orders of magnitude lower than that associated with NGF receptors on neurons ($K_D = 10^{-11}$M). The p75 receptor is a single peptide chain of about 400 amino acid residues, with a single membrane-spanning domain separating the NFG-binding extracellular domain from a shorter cytoplasmic domain and with no obvious consensus sequence for any known signal transduction mechanism (Large, et al., *Neuron*, 2:1123-1124 (1989)).

More recently, a new NGF receptor (referred to as p140$^{trkA}$ or simply trkA or trk) has been identified and cloned (Kaplan, et al., *Science*, 252:554-558 (1991); Klein, et al., *Cell*, 65:189-197 (1991)). The trk receptor is also a single peptide chain, somewhat larger than p75 (about 790 amino acids) with a single membrane-spanning domain. The intracellular C terminus of trk contains a tyrosine kinase consensus sequence; binding of NGF to trk induces autophosphorylation of trk and stimulates tyrosine kinase activity intracellularly (Kaplan, et al., *Science*, 252:554-558 (1991)).

It appears that the actions of NGF on NGF-responsive cells are mediated by the trk receptor (Kaplan, et al., *Science*, 252:554-558 (1991); Barker, et al., *Mol. Cell, Biochem.*, 110:1-15 (1992)). The role of the p75 receptor is less clear. It may be part of a multicomponent NGF receptor complex in some cell types, while perhaps being less critical in others (Bothwell, et al., *Cell*, 65:915-918 (1991); Meakin and Shooter, *TINS*, 15:323-331 (1992)). Of particular interest is a recent finding that glial cells, which express only p75 receptor and no trk, are capable of internalizing and degrading significant amounts of NGF, leading to the speculation that this is a regulatory mechanism of the amount of NGF available to neurons (Kahle and Hertel, *J. Biol. Chem.*, 267:13917-13923 (1992)). This would imply that blocking access of NGF to the p75 receptor will increase the amount of NGF available to neurons.

Effects of NGF on Neuronal Tumors

The importance of NGF in the formation of neuronal tumors has not been firmly established. Certain investigators believe that excessive synthesis of peptide growth factors or their receptors may lead to the transformation of the recipient cells (Levi-Montalcini, *Science*, 237:1154-1162 (1987)). In fact, it has been shown that brain tumors secrete a variety of growth factors, including NGF (Westermann, et al., *J. Neurochem.*, 50:1747-1758 (1988)), BDNF (Lichtor, et al., *Mol. Cell Neurosci.*, 2:168-171 (1991)) and their receptors (Prior, et al., *Pathol. Res. Pract.*, 185:332-338 (1989)). This suggests that agents that block the effects of NGF may be beneficial in the treatment of neuronal tumors.

On the other hand, NGF has been utilized as a reverse transforming agent to halt the progression of animal tumors of neurodegenic origin (Yaeger, et al., *Acta. Neuropathol.*, 83:624-629 (1992)).

Thus, there exists evidence to suggest that both blockade and stimulation of the effects of NGF may be beneficial for controlling the abnormal growth of tumors of neuronal origin. Any type of agent that modulates the interaction between NGF and its receptors may be considered as a potential antineoplastic.

Role of NGF in Inflammation

Recent studies document biological activities of NGF outside the central nervous system (CNS), acting as a cytokine that may be involved in inflammatory processes and hypersensitivity reactions. Very low concentrations of NGF act upon basophils to enhance release of histamine and modulate the formation of lipid mediators (Bischoff, et al., *Blood*, 79:2662-2669 (1992)). Higher concentrations of NGF induce degranulation of peritoneal mast cells (Pearce, Thompson, *J. Physiol.*, 372:379-393 (1986)). At this point, it is unclear what type of NGF receptor is responsible for these effects of NGF.

The p75 receptor may play a role in this activity and thus compounds that modulate the interaction between NGF and p75 may have some utility as antiinflammation or antiallergy agents.

Role of NGF in the Trophic Support of Sensory Neurons

All sympathetic and a subset of peripheral sensory neurons are dependent on NGF for survival, both in vitro and in vivo. For example, neutralization of NGF activity in newborn animals by administration of antibodies against NGF interferes with the normal development of sensory and sympathetic neurons (Rohrer, et al., *Development*, 103:545-552 (1988)). An important recent finding is that the p75 receptor plays a critical role in the development and function of peripheral sensory neurons. Thus, mutant mice containing a defective gene for p75 displayed markedly decreased sensory innervation in their extremities, while sympathetic neurons developed normally (Lee, et al., *Cell*, 69:737-749 (1992)). This finding suggests that the effects of NGF on some peripheral sensory neurons is mediated at least in part by p75 receptors. Thus, localized blockade of NGF-p75 interaction in the peripheral nervous system may lead to the degeneration of the sensory neurons innervating the point of blockade, and may be a viable option for pain control in certain patients, such as those with terminal stage cancer or those undergoing limb removal.

Screening of Drugs as trk Ligands

Under normal conditions, NGF-responsive neurons express higher levels of p75 than of trk (Perioso, Brooks, *Am. J. Pathol.*, 132:152-160 (1988)). Even though cloned cell lines have been engineered through molecular biology techniques to express exclusively 1 receptor or the other, these cell lines (e.g., PC12 or NIH-3T3) are usually derived from tumors and receptor expression levels tend to be much higher than in native neurons. A method that would allow the study of the interaction between NGF and trk in a culture of native neurons (such as hippocampal neurons) expressing normal levels of p75 and trk receptors, without interference from the p75 receptors, would be very useful in a discovery program aimed at identifying ligands for the trk receptor.

Neurotrophins

NGF is a member of a family of related neurotrophic peptides, the neurotrophins, all with a high degree of similarity in terms of their molecular weight and amino acid sequence. Other representative members of the neurotrophins include Brain Derived Neurotrophic Factor (BDNF) and neurotrophin-3 (NT-3). While these peptides are selectively expressed in discrete areas of the brain of mammals, they all seem to bind to the same p75 receptor as NGF (Squinto, et al., *Cell*, 65:885-893 (1991)), and they seem to possess neurotrophic activity at well-defined populations of neurons. For instance, BDNF exerts neurotrophic effects on substantia nigra dopaminergic neurons (Knuesel, et al., *Proc. Acad. Sci. USA*, 88:961-965 (1991)). Since degeneration of these neurons is directly responsible for Parkinson's disease (PD), it is conceivable that BDNF is useful in the treatment of this devastating disease. Since all the members of the neurotrophin family interact with the p75 receptor, the same arguments made above for compounds that modulate NGF/p75 interaction can also be made of compounds that modulate BDNF/p75 or NT-3/p75 binding.

AD, PD, and drug-induced peripheral neuropathies are but a few of the many neurodegenerative conditions that might be amenable to neurotrophic treatment. However, as mentioned above, NGF and related neurotrophins are large peptides (around 120 amino acids), which large size makes them unlikely therapeutic candidates. In addition to the lack of a ready source of endogenous peptide(s), these compounds possess very poor pharmacokinetic parameters (e.g., poor oral absorption, short in vivo half-life) and administration to the target organs also represents a major problem. One solution requires the use of cerebral implants of genetically engineered cells (Rosenberg, et al., *Science*, 242:1575-1578 (1988)) or intracerebral pumping devices for continuous infusion of the peptide (Powell, et al., *Brain Res.*, 515:309-311 (1990)). For these reasons, it would be extremely useful to identify novel compounds with physicochemical properties different from the neurotrophins but still able to interact with the neurotrophins' receptors. The ideal compounds would be nonpeptides, since this would enhance in vivo half-life. The nonpeptides would be much smaller in molecular size than the endogenous peptides, as this would be expected to enhance oral absorption and CNS penetration. The present invention describes the identification of such a group of compounds that bind to NGF and very specifically prevent its binding to the p75 receptor without affecting its interaction with trk. These agents may be useful in stimulating neuronal regeneration, as antiinflammation and antiallergy therapeutics, as analgesics, antineoplastics, and as screening tools for compounds with NGF-like activity at trk receptors. The selective interaction of these agents with NGF suggests that radiolabeled derivatives of these agents will be useful as diagnostic tools for neurodegenerative disorders. Thus, such radiolabeled derivatives can be administered to a live human or animal subject.

Administration can be systemic or localized to a specific organ. After a predetermined period of time, the compounds will be expected to bind to NGF in the subject's body. Utilizing the compound's radioisotope as a marker, it should then be possible to evaluate the levels of NGF in the subject, which may have certain diagnostic value in situations where neurodegeneration is associated with a decrease in endogenous levels of NGF.

SUMMARY OF INVENTION

In one aspect, the invention concerns pyrazoloquinozole compounds that have use in their capacity to bind NGF in a specific manner that prevents it from interacting with the p75 receptor while leaving intact its ability to interact with the trk receptor, and thus are useful in dosage form in the treatment of CNS neurodegenerative disorders such as Alzheimer's disease, Parkinson's disease, Huntington's chorea, and the like, and PNS neurodegenerative disorders such as drug-induced peripheral neuropathies and the like.

More particularly, the invention relates to pyrazoloquinazolone compounds of Formula I

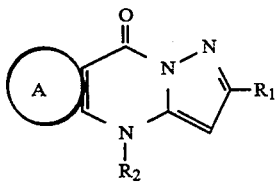

and salts thereof, wherein

is a moiety selected from

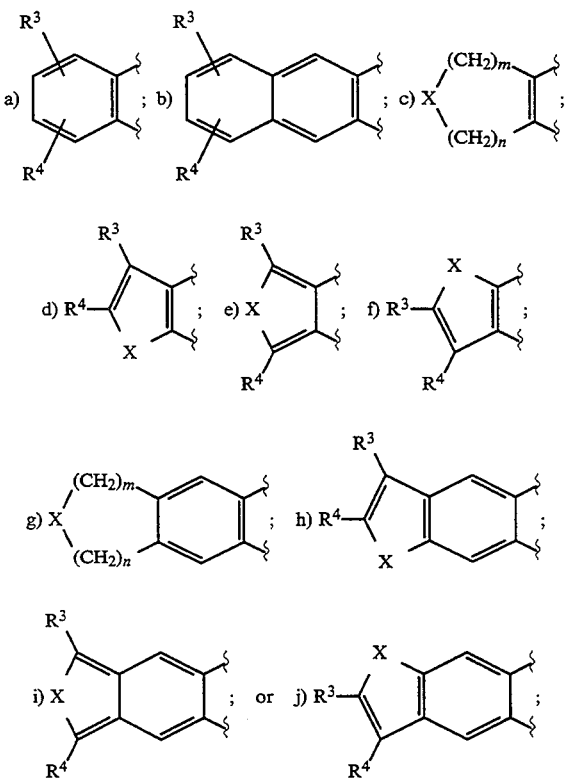

$R^1$ is an acid group selected from —COOH, —SO$_3$H,

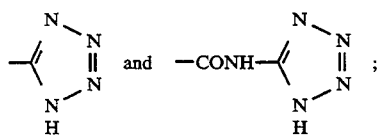

$R^2$ is a member selected from H, alkyl, arylalkyl, alkenyl and alkynyl;

$R^3$ and $R^4$ can independently be H, alkyl, aryl, —COOH, —CONH$_2$, —CO-NH-aryl, —CO-NH-heteroaryl, —CO-NH-alkyl, —CO-NH—(CH$_2$)$_p$-CO$_2$H, —CO-NH-arylalkyl, —SO$_2$-NH-alkyl, —SO$_2$-NH-aryl, —SO$_2$-NH-heteroaryl, —SO$_2$-NH-arylalkyl, —NH-SO$_2$-alkyl, —NH-SO$_2$-aryl, —NH-SO$_2$ heteroaryl, —NH-SO$_2$-arylalkyl, —NH$_2$, —NH-CO-alkyl, —NHCO-aryl, —NH-CO-heteroaryl, —NH-CO-(CH$_2$)$_p$-CO$_2$H, —NHCO-arylalkyl, or —NHCO-N(R$^5$)R$^6$ wherein R$^5$ and R$^6$ can independently be H, alkyl or aryl;

m and n can independently be 0, 1, or 2; p can be 1–6; and X is O, S or NH;

provided that, for a compound having moiety a):
1) wherein $R^1$ is COOH and $R^2$ is H or CH$_3$, $R^3$ and $R^4$ represent a combination other than 7-CH$_3$ and H, 7-NH$_2$ and H, 7-CH$_3$CONH and H, 7-C$_6$H$_5$CONH and H, H and H, —NH$_2$ and H, H and 5-CH$_3$, 7-COOH and H, and H and 6-COOH;
2) wherein $R^1$ is

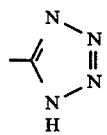

and $R^2$ is H or $CH_3$, $R^3$ and $R^4$ represent a combination other than H and H;
3) wherein $R^1$ is

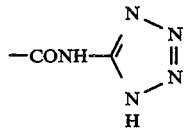

and R2 is H or
$CH_3$, $R^3$ and $R^4$ represent a combination other than H and H; and
4) wherein $R^1$ is

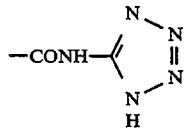

and $R^2$ is H, $R^3$ and $R^4$ represent a combination other than H and 5-$CH_3$.

Preferred compounds are those wherein $R^1$ is selected from the group consisting of —COOH,

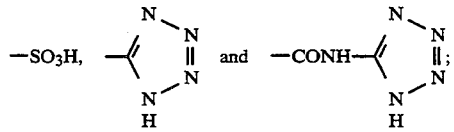

$R^2$ is H or alkyl; and

is a moiety selected from

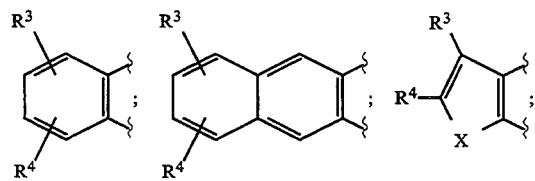

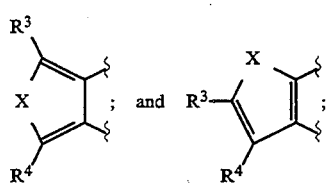

Especially preferred compounds are those wherein $R^1$ is selected from the group consisting of —COOH,

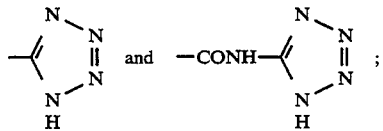

$R^2$ is H or methyl; and

is a moiety selected from

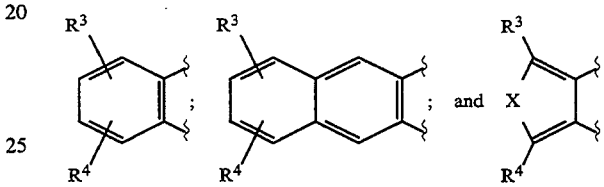

1 of $R^3$ and $R^4$ is H and the other is selected from H, —$NH_2$, —NHCO-aryl, —NHCO— $(CH_2)_p$—COOH, and COOH.

DETAILED DESCRIPTION

In the compounds of Formula I, the term "alkyl" is intended to mean a hydrocarbon moiety which may be straight, branched, or cyclic in configuration, having from 1 to 6 carbon atoms, including, for example, methyl, ethyl, n-propyl, isopropyl, n-butyl, sec-butyl, isobutyl, n-pentyl, n-hexyl, and the like.

The term "aryl" means an aromatic radical which is a phenyl group or a phenyl group substituted by 1 to 4 substituents selected from alkyl, alkoxy, carboxy, thioalkoxy, hydroxy, lower acyloxy, amino, —NHCO-$R_2$, where $R_2$ is as defined above, halogen, or trifluoromethyl.

The term "heteroaryl" means a "5- or 6-membered heteroaromatic ring" including, for example: 2-, 3-, or 4-pyridinyl, 2-, 4-, or 5-pyrimidinyl, 2-pyrazinyl, 2- or 3-furanyl, 2- or 3-thienyl, 2-, 4-, or 5-imidazolyl, 2-, 4-, or 5-thiazolyl, unsubstituted or substituted by halogen, lower alkyl, hydroxy, lower
acyloxy, lower alkoxy, amino, or

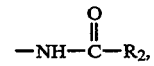

wherein $R_2$ is lower alkyl.

"Alkoxy" and "thioalkoxy" are O-alkyl or S-alkyl of from 1 to 6 carbon atoms as defined above for "alkyl".

"Lower acyloxy" is

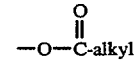

of from 1 to 6 carbon atoms as defined above for "alkyl".

"Halogen" is fluorine, chlorine, bromine, or iodine.

The tetrazole ring exists in two tautomeric forms

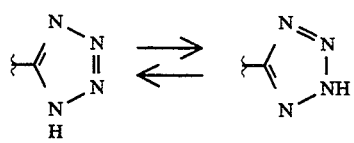

and both are considered to be included when only one is shown.

The term "salts" is intended to mean salts formed by the addition of a base with those compounds of the invention capable of forming a salt, such as those compounds containing a carboxy or tetrazole group. Typical salts would be inorganic such as sodium, potassium, calcium, magnesium, etc; organic salts, such as ammonium, triethylammonium, trimethylammonium, triethanolammonium, dimethylammonium, and the like. The preferred salts are relatively nontoxic, thus pharmaceutically acceptable salts, preferably the sodium salt. Some of the compounds of this invention may form acid addition salts with strong acids, such as hydrochloric, nitric, phosphoric, sulfuric, hydrobromic, and the like, as well as salts derived from nontoxic organic acids, such as oxalate, acetate, malonate, tartrate, and the like.

Certain of the compounds of this invention are capable of existing in the form of hydrates or solvates. For the purposes of this invention, these other forms of the compounds are considered equivalent to the nonhydrated or nonsolvated compounds and are intended to be encompassed within the scope of the invention.

Certain ones of these compounds are known in the literature for their effects as antiallergic agents: Sircar, et al., *J. Med. Chem.*, 24:735–742 (1981); Sircar, et al., *J. Heterocycl. Chem.*, 18:117–121 (1981); U.S. Pat. No. 4,247,555, incorporated herein by reference. The compounds may be prepared by methods that are illustrated in the following Schemes I, II, and III.

SCHEME I

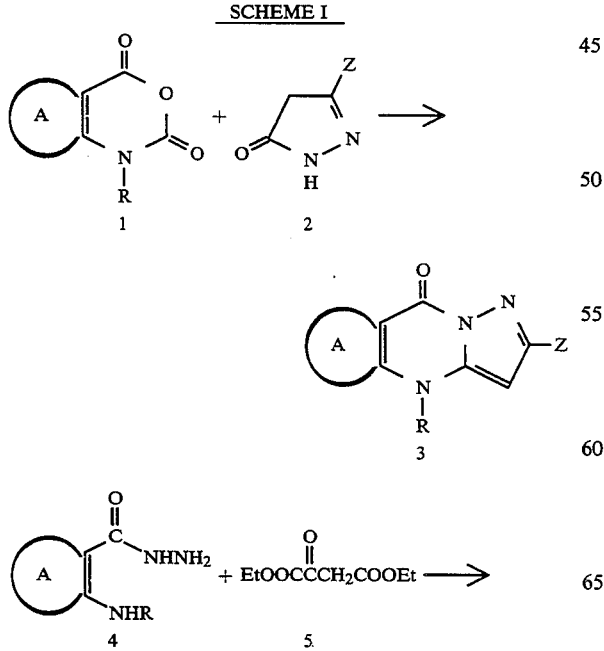

-continued
SCHEME I

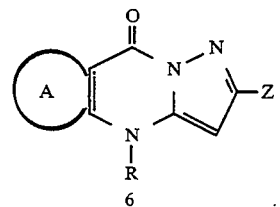

SCHEME II

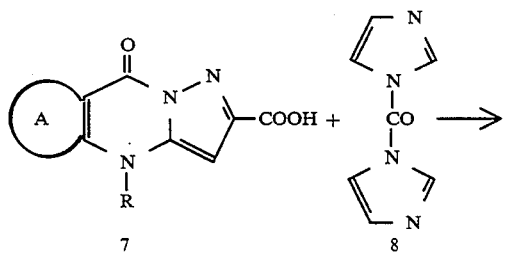

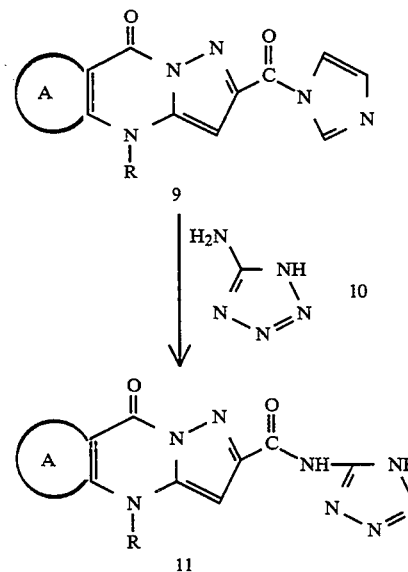

SCHEME III

-continued
SCHEME III

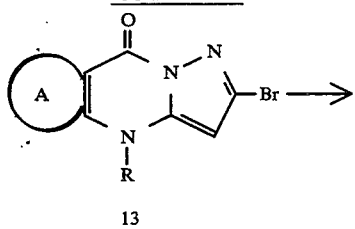

13

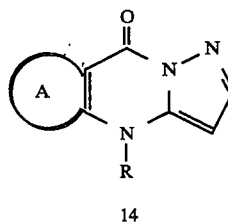

14

In Scheme I, ring opening of the isotoic anhydrides (1) with 5-substituted pyrazol-3-ones (2) gives the pyrazoloquinazolones (3). The acids (3; Z=COOH) are prepared by hydrolysis of the esters (3; Z=COOEr). The acids (3; Z=COOH) are converted to the tetrazoles via the sequence of the acid (3; Z=COOH) to the amide to the
nitrile and then to the tetrazoles

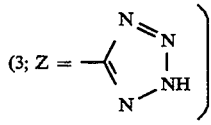

by methods known in the art.

In Scheme II, the tetrazol-5-ylamides (11) are made from the acids (7) and 1H-tetrazol-5-amine (10), using 1,1'-carbonyldiimidazole (8) as a coupling agent. The intermediates (9) may be isolated and on treatment with 1H-tetrazol-5-amine (10) in DMF give the desired tetrazol-5-ylamides (11). The NH series (6, R=H) can be prepared from the acid hydrazide (4, R=H) by reacting the same with sodium diethyloxalacetate. The compounds (6, 9, 11, and 15, R=H) can be alkylated with alkyl halides and sodium carbonate in DMF to give 3 (R=alkyl).

In Scheme III, the acids (7) are converted to the amines (12) employing a Curtius rearrangement by reaction with the azide (PhO)$_2$P(O)N$_3$ in triethylamine and methylene chloride followed by a hydrolyric workup in a medium such as t-butanol, again followed by HCl hydrolysis. The amines (12) are diazotized employing NaNO$_2$ and HCl to form the diazonium salt followed by the Sandmeyer reaction employing CuBr in HBr with heating to form the bromo compounds (13). The bromo compounds are reacted with n-butyllithium or t-butyllithium to exchange the halogen for metal, followed first by reaction of the organometallic intermediate with ClS(O$_2$)X (where X=Cl or O-alkyl) and then by acidic hydrolysis (e.g., 10% HCl) to provide the desired sulfonic acid analogues (14).

As indicated, compounds of this invention are useful pharmaceutical agents. More specifically, the compounds are useful as active agents in the treatment of neurodegenerative disorders of the CNS such as Alzheimer's disease, Parkinson's disease, Huntington's chorea, and similar disorders, and neurodegenerative disorders of the PNS, such as drug-induced peripheral neuropathies and the like. The compounds are also useful as active agents in the treatment of tumors of neuronal origin, in the treatment of allergy and inflammation, as analgesic agents, as tools in the screening for agents with neurotrophic and antineurotrophic activity, and as diagnostic agents for neurodegenerative disorders by determining, in a live animal or patient and utilizing a radiolabeled form of the compounds, the endogenous levels of NGF or other neurotrophins in said subject.

The compounds may be administered orally or parenterally or by direct injection into the target organ. The usual human dosage ranges, for a 80-kg subject, from about 1 mg to about 1 g per day (0.01 mg to 10 mg per kg of weight per day), preferably 10 mg to 100 mg per day (0.1 mg to 1.0 mg per kg of weight per day), optionally in divided portions.

The above employed pharmaceutical compositions are produced by formulating a compound of the foregoing formula (active ingredient) in dosage unit form with a pharmaceutical carrier. Some examples of dosage unit forms are tablets, capsules, lozenges, and pills; as well as powders and aqueous and nonaqueous oral solutions and suspensions and parenteral solutions, packaged in containers containing either 1 or some larger number of dosage units and capable of being subdivided into individual doses by such means as measurement into a teaspoon or other standard container. Some examples of suitable pharmaceutical carrier, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc, stearic acid; magnesium stearate; vegetable oils such as peanut oil, cottonseed oil, sesame oil, olive oil, corn oil, and oil of theobroma; propylene glycol; glycol; glycerine, sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 2 mg to 1.0 g of the active ingredient per dosage unit so that the entire amount to be administered during a day can be made up from a reasonable number of dosage units.

BRIEF DESCRIPTION OF DRAWINGS

The NGF binding activity of the compounds of this invention has been determined using an assay described as follows and as illustrated in FIGS. 1–6.

DESCRIPTION OF THE ASSAY USED TO DETERMINE THE ABILITY OF NOVEL COMPOUNDS TO BLOCK THE BINDING OF NGF TO THE P75 RECEPTOR

Assays of novel compounds are performed by measuring the compounds' ability to inhibit the binding of NGF to the NGF p75 receptor, using a truncated form (Residues 1-222, molecular weight=56 KDa) of the p75 receptor, originally obtained from Chiron Corporation, Emeryville, Calif., but also commercially available from Austral Biologicals, Inc. (San Diego, Calif.), on plastic 96-well microtiter plates (Immulon 11 Dynatech). The wells are coated with 50 μL/well of 20 μg/mL streptavidin in a diphosphate buffer solution (DPBS). The plates are then incubated at room temperature for 6 hours. The excess streptavidin is then poured out, the wells are washed with a 0.1% solution of bovine serum albumin (BSA) in DPBS. To each well is then added 50 μg/mL of a DPBS solution containing the truncated p75 receptor, which has previously been reacted with biotin by standard procedures. The plates are then incubated at room temperature for 2 hours and washed with 0.2% BSA/DPBS. To each well is added 98 μL of 2 nM $^{125}$I-NGF, followed by 2 μL/well of a concentration of test compound that is 50 times greater than the desired final test concentration. The plates are incubated for 2 hours at room temperature. The assay is read as the $IC_{50}$, the concentration of compound that blocks 50% of the binding of $^{125}$I-NGF to the p75 receptor.

Figure 1:
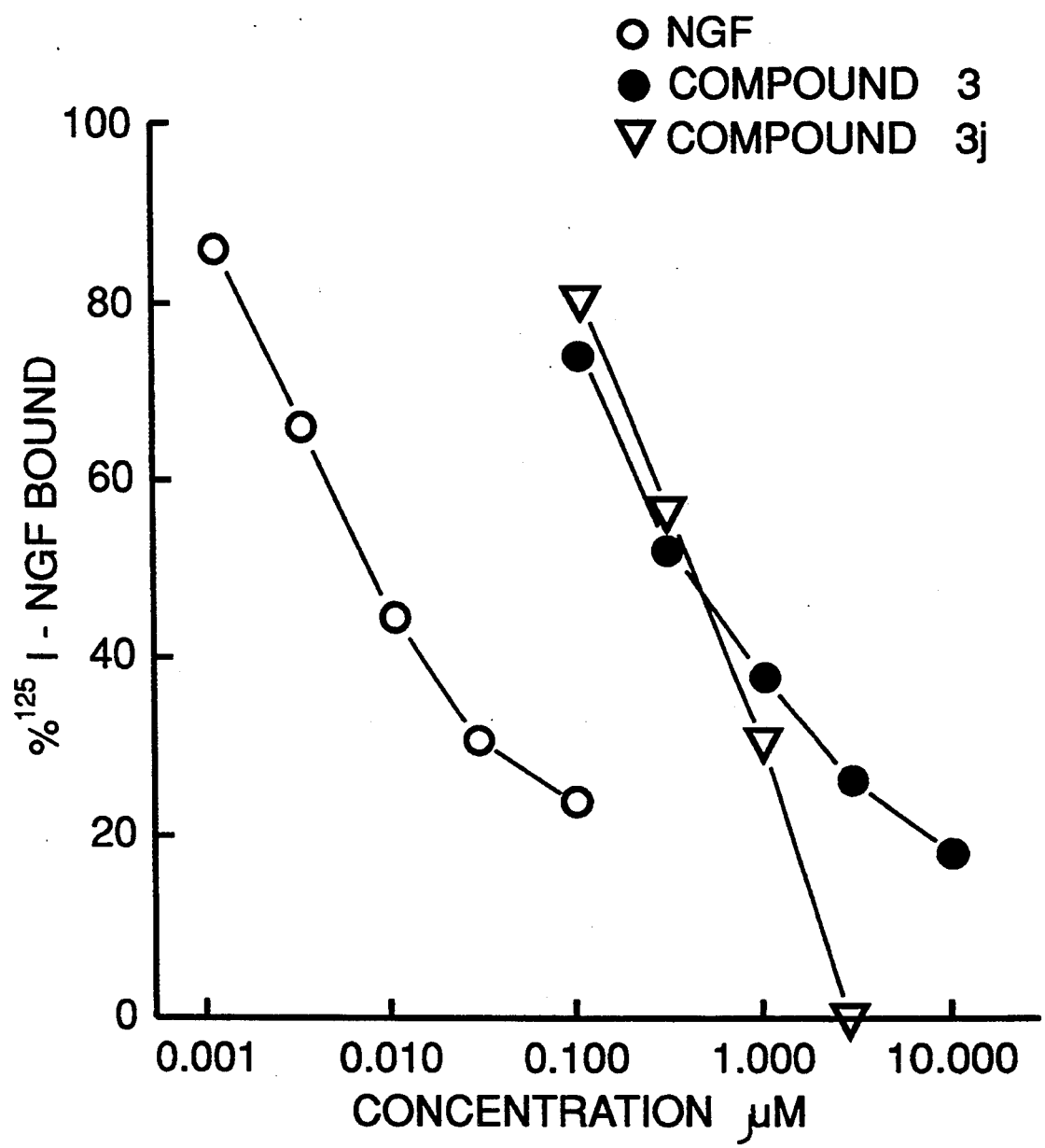
Figure 2:
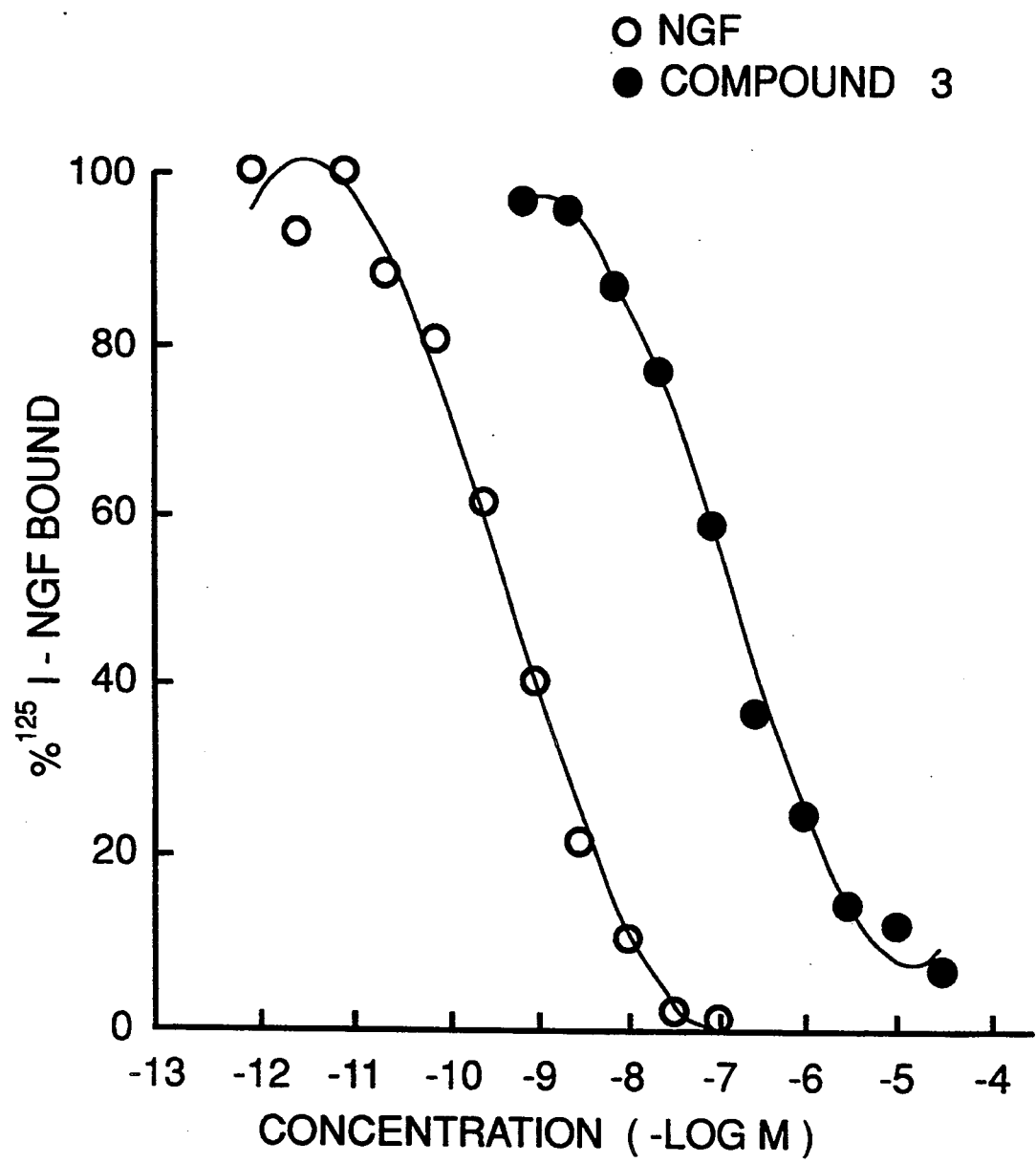
Figure 3:
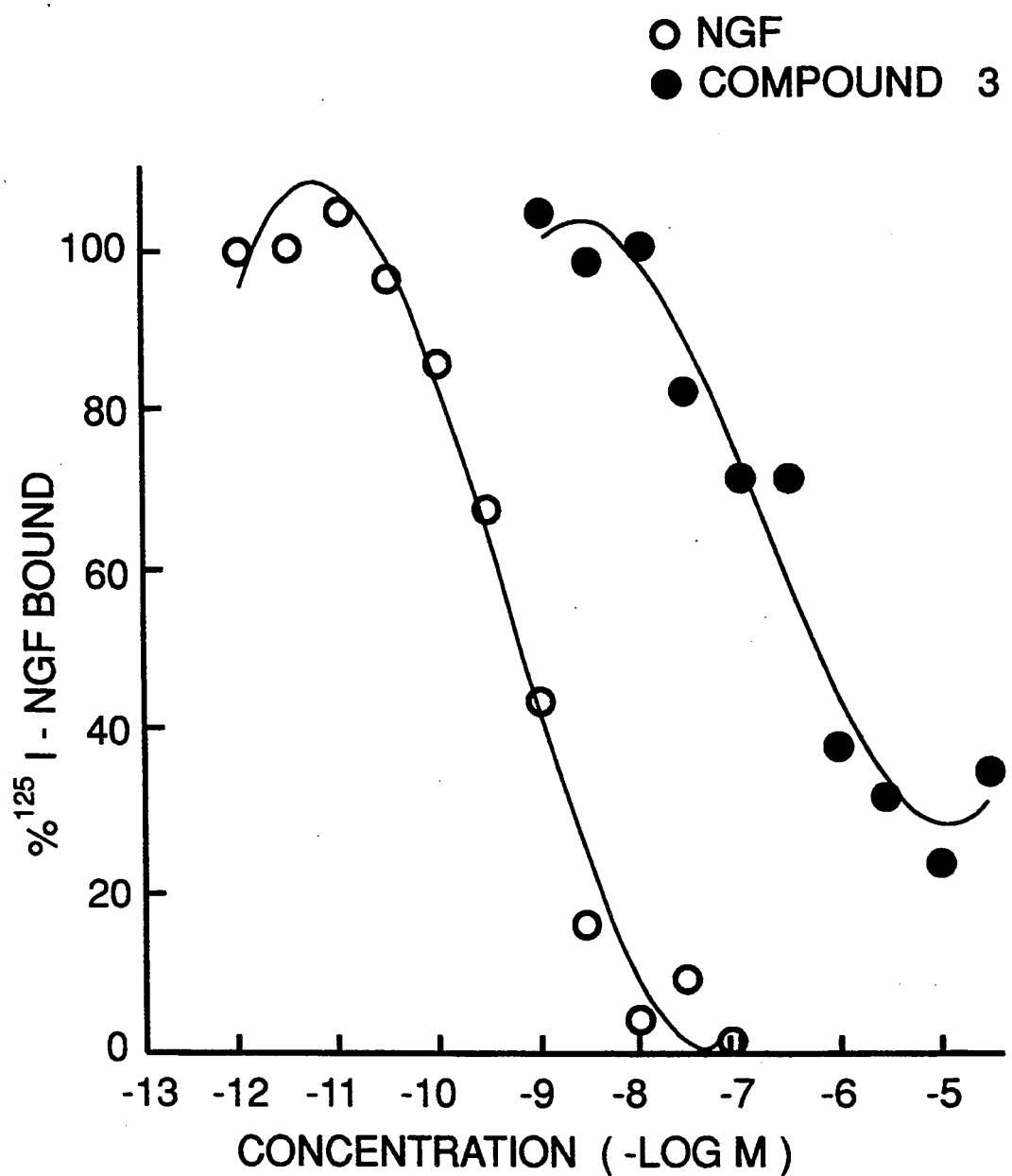
Figure 4:
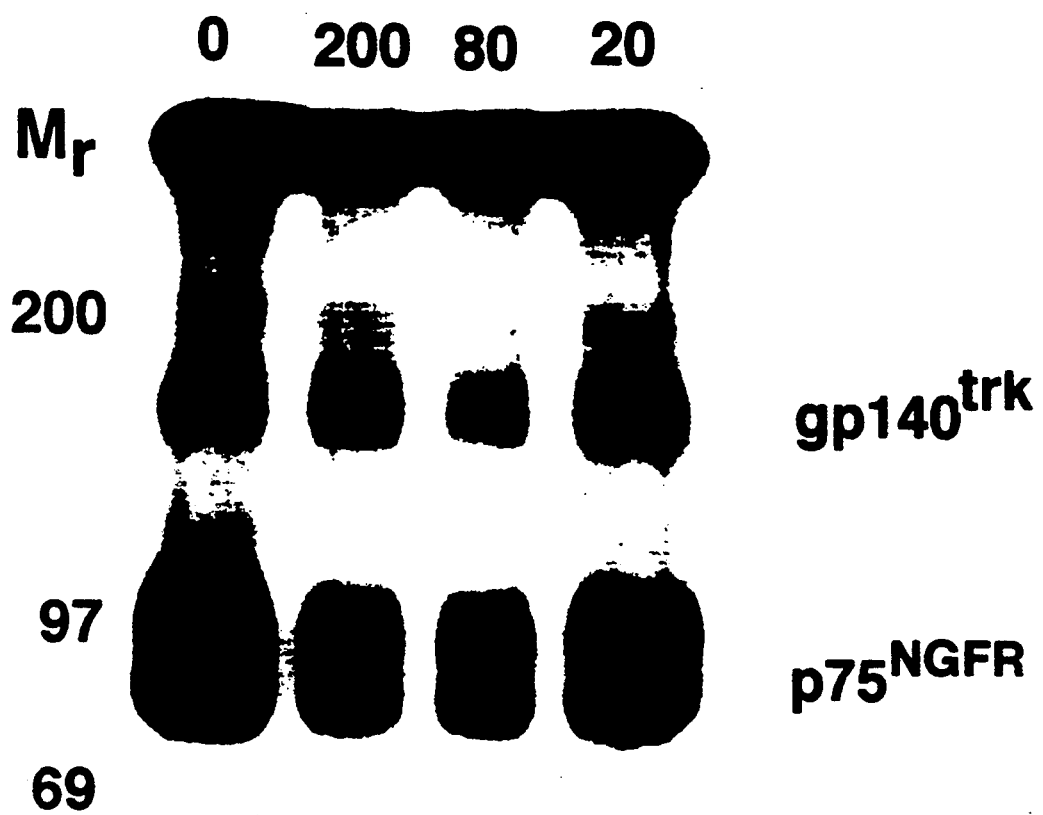
Figure 5:
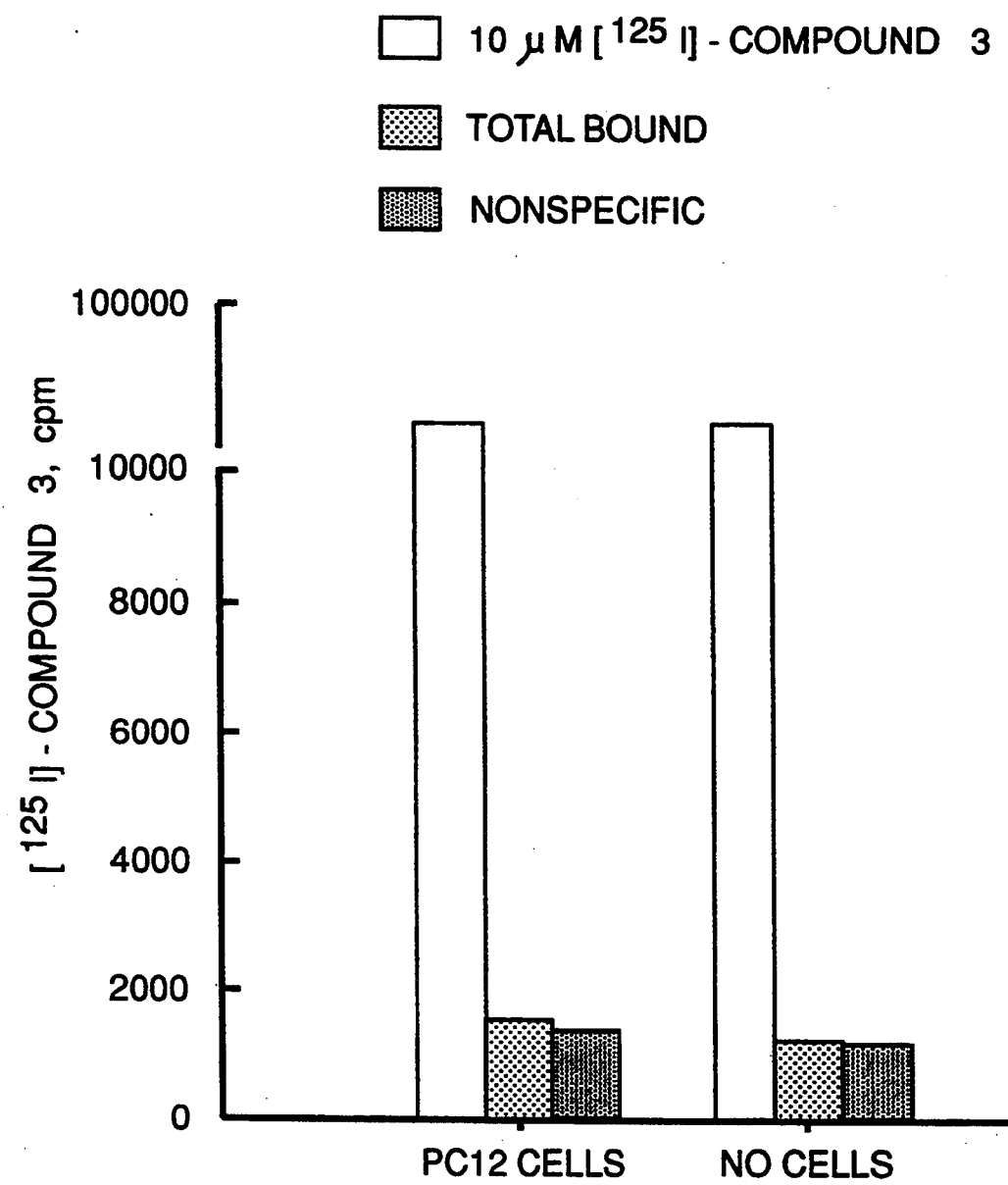
Figure 6:
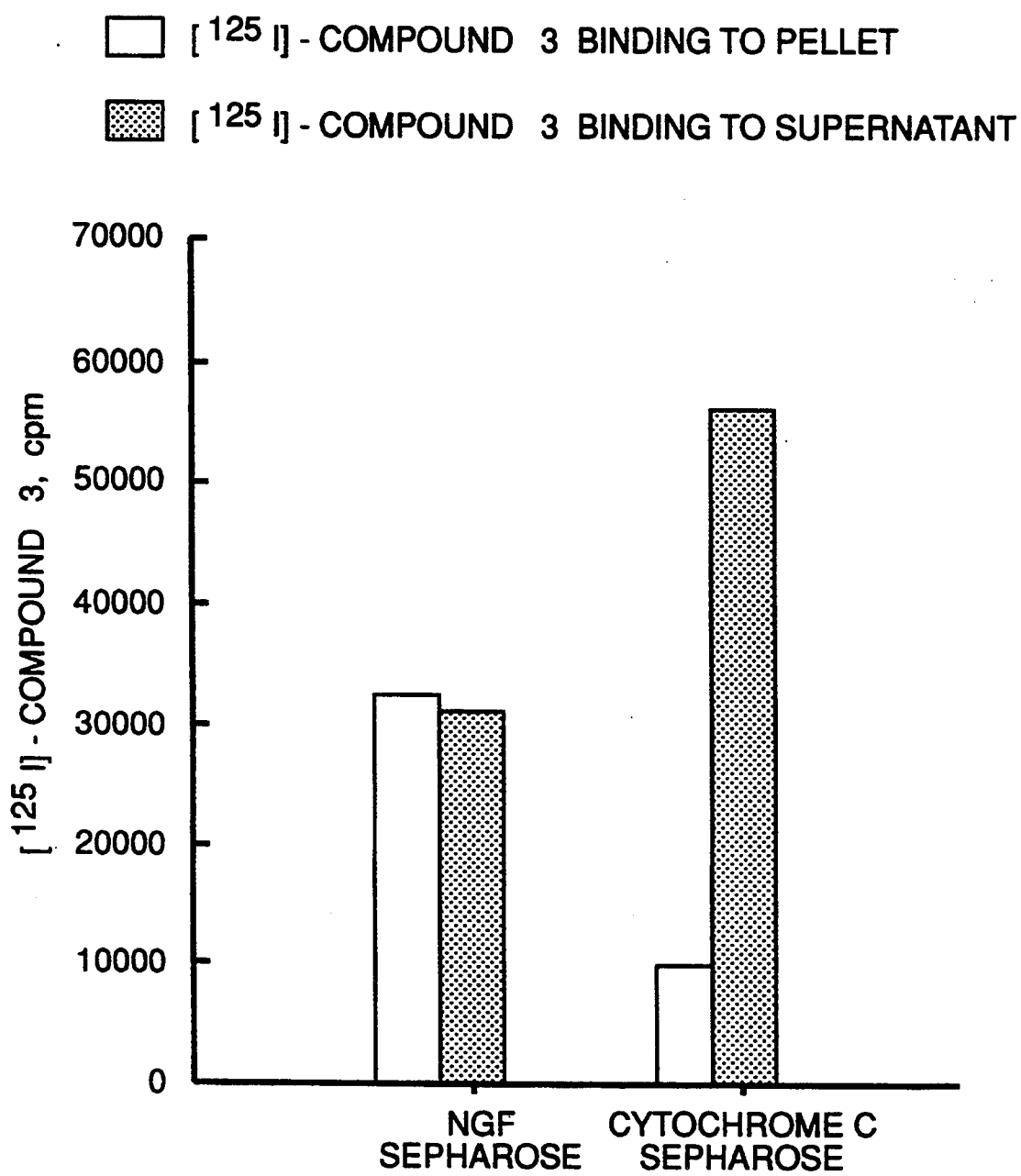

In principle, a compound may inhibit the binding of NGF to the p75 receptor by interacting with either protein. The compounds of the present invention are studied further as exemplified here with the compound of Example 3. As seen in FIG. 1, Compound 3 prevents the binding of $^{125}$I-NGF to the extracellular domain of p75. FIG. 2 shows that Compound 3 completely prevents binding of $^{125}$I-NGF to full length p75 receptor expressed in CHO cells that lack trk expression. However, as shown in FIG. 3, Compound 3 can only block about 80% of the $^{125}$I-NGF binding in PC12 cells that express both p75 (about 80% of the total NGF receptor number) and trk (about 20% of the total NGF receptors). That Compound 3 selectively blocks the ability of NGF to interact with p75 without affecting the NGF-trk interaction is further illustrated in FIG. 4, which shows that Compound 3 can inhibit the crosslinking of $^{125}$I-NGF to p75 but not to trk. Utilizing a radioiodinated derivative of Compound 3 (corresponding to Example 3j), FIG. 5 illustrates that Compound 3 does not bind to NGF receptors directly. Rather, as illustrated in FIG. 6, there exists a specific interaction between Compound 3 and NGF (in this case bound to a sepharose support).

These results illustrate that the compounds of the present invention recognize very specifically a region of the NGF molecule that is absolutely essential for binding to p75 but is apparently not important for binding to trk.

The activity of preferred compounds is given in Table I.

TABLE I

Inhibition of $^{125}$I-NGF Binding to the Extracellular Domain of the p75 Receptor

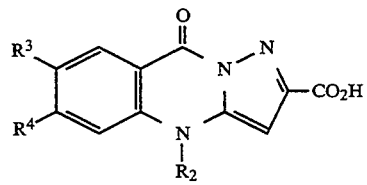

| Example | R2 | R3 | R4 | Concentration ($IC_{50}$, nM) |
|---|---|---|---|---|
| 1* | Me | $NH_2$ | H | 1900 |
| * | Me | $CH_3CONH$ | H | 1700 |
| 3* | Me | PhCONH | H | 228 |
| * | Me | H | H | 30800 |
| * | Me | Me | H | 9700 |
| * | H | H | $CO_2H$ | 1100 |
| * | H | $NH_2$ | H | 338 |
| * | H | Me | H | 12900 |
| 3b | Me | 4-Me-PhCONH | H | 180 |
| 3c | Me | 4-MeO-PhCONH | H | 10000 |
| 3d | Me | 4-Cl-PhCONH | H | 250 |
| 3f | Me | 3,4-$Cl_2$-PhCONH | H | 844 |
| 3j | Me | 4-I-PhCONH | H | 472 |
| 3k | Me | 4-$NO_2$-PhCONH | H | 229 |
| 3l | Me | 4-t-Bu-PhCONH | H | 862 |
| 3n | Me | 4-$CF_3$-PhCONH | H | 2568 |
| 3p | Me | 3-Me-PhCONH | H | 748 |
| 3r | Me | 2-Me-PhCONH | H | >10000 |
| 3g | Me | PhNHCONH | H | 3876 |
| 3e | Me | $PhCH_2CONH$ | H | 568 |
| 3h | Me | $PhCH_2CH_2CONH$ | H | 1709 |
| 3q | Me | 4-Ph-PhCONH | H | 222 |
| 3a | Me | 2-Thienyl-CONH | H | 690 |
| 3i | Me | 2-Naphthyl-CONH | H | 431 |
| 3m | Me | Adamantyl-CONH | H | 2231 |
| 3s | Me | 4-F-PhCONH | H | 266 |
| 3t | Me | 4-COOH-PhCONH | H | 166 |
| 3u | Me | (3-I-4-Me)-PhCONH | H | ~200 |
| 3v | Me | $HOOC-CH_2-CONH$ | H | 1154 |

TABLE I-continued

Inhibition of $^{125}$I-NGF Binding to the Extracellular Domain of the p75 Receptor

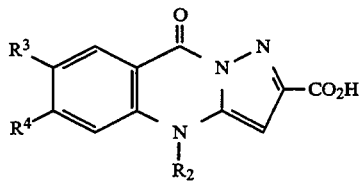

| Example | R$_2$ | R$_3$ | R$_4$ | Concentration (IC$_{50}$, nM) |
|---------|-------|-------|-------|-------------------------------|
| 3w | Me | HOOC—CH$_2$CH$_2$—CONH | H | 116 |
| 3x | Me | HOOC—CH$_2$CH$_2$CH$_2$—CONH | H | 36 |
| 7  | Me | 4-Me-PhCONH | H | 1159 |

*indicates compounds previously described as antiallergy agents (Sircar, et al., J. Med. Chem., 24:735–742 (1981); Sircar, et al., J. Heterocylic. Chem., 18:117–121 (1981); U.S. Pat. No. 4,247,555)

A common problem in performing competitive binding assays between NGF (or one of the related neurotrophic factors BDNF, NT-3, NT-4, NT-5, etc) and the corresponding signal-transducing receptor trK (or trkB, trkC, etc) is that cell lines that express high levels of the trk receptors exclusively, in the absence of p75 receptors, are not readily available. For instance, the commonly used PC12 cell line expresses several times more p75 receptor than trk receptors. Thus, competitive binding assays between NGF and PC12 cells or cell membranes from PC12 cells reflect binding of NGF to both types of receptors. Since trk is the signalling receptor, it is desirable to screen compounds for their ability to bind to trk, which requires the neutralization of the p75 receptor. The compounds of the present invention, by binding to NGF and selectively preventing it from binding to p75, allow NGF to bind to trk exclusively. Thus, a competitive binding assay between radiolabeled NGF and PC12 cells (or any other cell line that expresses both p75 and trk) performed in the presence of one of the compounds of the present invention, will reflect the binding of NGF to trk exclusively. Such an assay can be used to screen large numbers of compounds for their ability to bind to trk. Some of the compounds may also activate trk and thus possess neurotrophic activity similar to NGF itself.

The invention is further illustrated and the best mode is described in the following examples.

EXAMPLE 1

7-Amino-4,9-dihydro-4-methyl-9-oxopyrazolo[5,1-b]-quinazoline-2-carboxylic acid

The procedure of Sircar, et al., (J. Med. Chem., 24:735–742 (1981)) was followed. A mixture of 5-amino-2-methylaminobenzoic acid hydrazide (35.05 g, 0.194 mol) and 95% diethyl oxalacetate, sodium salt (47.33 g, 0.214 mol, Aldrich Chemical Co.) in 1 L of water was refluxed for 2 hours. The dark solution was cooled to room temperature and sodium carbonate (22.68 g, 0.214 mol) was added. The solution was refluxed for 1 hour, then allowed to cool to room temperature overnight. A small amount of solid formed. The mixture was filtered through a pad of Celite, the filtrate was cooled and acidified by dropwise addition of 10% hydrochloric acid. At a pH of about 4, a solid formed, the mixture was filtered, and the yellow-green solid was washed with water and vacuum-dried to give 29.65 g (59%) of the title compound, mp 249°–252° C., dec.

EXAMPLE 2

7-Amino-4,9-dihydro-4-methyl-9-oxopyrazolo[5,1-b)-quinazoline-2-carboxylic acid, ethyl ester A mixture of 7-amino-4,9-dihydro-4-methyl-9-oxopyrazolo[5,1-b]quinazoline-2-carboxylic acid (8.03 g, 31.10 mmol, Example 1) in 600 mL of ethanol was saturated with hydrogen chloride gas for 20 minutes. The mixture was then refluxed for 12 hours, cooled, concentrated (to remove most of the ethanol), and partitioned between saturated sodium bicarbonate solution and chloroform (500 mL of each). Some solid would not dissolve into either phase. The mixture was filtered, giving 7.19 g (81%) of the title compound as a yellow solid, mp 258°–260° C., dec. The chloroform extract did contain more product, although not as clean.

EXAMPLE 3

7-(Benzoylamino)-4,9-dihydro-4-methyl-9-oxopyrazolo-[5,1-b]quinazoline-2-carboxylic acid To a solution of 7-amino-4,9-dihydro-4-methyl-9-oxopyrazolo[5,1-b]quinazoline-2-carboxylic acid, ethyl ester (0.75 g, 2.62 mmol, Example 2) and triethylamine (0.46 mL, 3.30 mmol) in 500 mL of methylene chloride was added dropwise a solution of benzoyl chloride (0.34 mL, 2.93 mmol) in 50 mL of methylene chloride at room temperature. A yellow solid slowly formed. The mixture was stirred at room temperature for 12 hours and filtered. The yellow solid was washed with methylene chloride and diethyl ether and vacuum-dried, affording the title compound as its ethyl ester, mp 275°–278° C., dec.

A suspension of the above ethyl ester in THF:water (—1:1) containing 2.5 equivalents of sodium carbonate was refluxed under N$_2$. After 2 hours, most of the solid was in solution. The hot suspension was filtered through a pad of Celite, and the filtrate was cooled and acidified with 1N hydrochloric acid. At a pH of about 4 to 4.5, yellow solid precipitated. The mixture was stirred at room temperature for 2 hours, cooled, and filtered. The solid was washed with water and vacuum-dried to give the title compound as a yellow solid, mp 243°–245° C., dec.

In a process analogous to Example 3, using 7-amino-4,9-dihydro-4-methyl-9-oxopyrazolo[5,1-b]-quinazoline-2-carboxylic acid, ethyl ester and the appropriate acid chlorides, the corresponding compounds were prepared as follows:

EXAMPLE 3a 4,9-Dihydro-4-methyl-9-oxo-7-[(2-thienylcarbonyl)amino]pyrazolo[5,1-b]quinazoline-2-carboxylic acid, mp 220° C., dec

EXAMPLE 3b 4,9-Dihydro-4-methyl-9-oxo-7-[(4-methylbenzoyl)amino]-pyrazolo[5,1-b]quinazoline-2-carboxylic acid, mp 264°–266° C., dec

EXAMPLE 3c 4,9-Dihydro-4-methyl-9-oxo-7-[(4-methoxybenzoyl)amino]-pyrazolo[5,1-b]quinazoline-2-carboxylic acid, mp 272°–274° C. dec

EXAMPLE 3d

7-[(4-Chlorobenzoyl) amino]-4,9-dihydro-4-methyl-9-oxopyrazolo [5,1-b]quinazoline-2-carboxylic acid, mp 301–305° C., dec

EXAMPLE 3e 4,9-Dihydro-4-methyl-9-oxo-7-[(phenylacetyl)aminol]-pyrazolo[5,1-b]quinazoline-2-carboxylic acid, mp 270°–272° C., dec

EXAMPLE 3f

7-[(3,4-Dichlorobenzoyl)amino]-4,9-dihydro-4-methyl-9-oxopyrazolo[5,1-b]quinazoline-2-carboxylic acid, mp >300° C.

EXAMPLE 3g 4,9-Dihydro-4-methyl-9-oxo-7-[(phenylamino) carbonyl]-amino]pyrazolo-[5,1-b]quinazoline-2-carboxylic acid, mp >305° C.

EXAMPLE 3h 4,9-Dihydro-4-methyl-9-oxo-7[(1-oxo-3-phenylpropyl) -amino]pyrazolo [5,1-b]quinazoline-2-carboxylic acid, mp 246°–247° C., dec

EXAMPLE 3i 4,9-Dihydro-4-methyl-7-[-2-naphthalenylcarbonyl)amino]-9-oxopyrazolo[5,1-b]quinazoline-2-carboxylic acid, mp 273°–278° C., dec

EXAMPLE 3j 4,9-Dihydro-7-[(4-iodobenzoyl) amino]-4-methyl-9-oxopyrazolo[5,1-b]quinazoline-2-carboxylic acid, mp >280° C.

EXAMPLE 3k 4,9-Dihydro-4-methyl-7-[(4-nitrobenzoyl)amino]-9-oxopyrazolo[5,1-b]quinazoline-2-carboxylic acid, mp >280° C.

EXAMPLE 3l

7-[(4-tert-Butylbenzoyl)amino]-4,9-dihydro-4-methyl-9-oxopyrazolo[5,1-b]quinazoline-2-carboxylic acid, mp >295° C.

EXAMPLE 3m 4,9-Dihydro-4-methyl-9-oxo-7-[(tricyclo[3.3.1.1$^{3,7}$]-dec-1-ylcarbonyl) amino]pyrazolo[5,1-b]quinazoline-2-carboxylic acid, mp 293°–303° C., dec

EXAMPLE 3n 4,9-Dihydro-4-methyl-9-oxo-7-[[(4-trifluoromethyl)-benzoyl]amino]pyrazolo [5,1-b]quinazoline-2-carboxylic acid, mp >310° C.

EXAMPLE 3p 4,9-Dihydro-4-methyl-7-[(3-methylbenzoyl)amino]-9-oxopyrazolo[5,1-b]quinazoline-2-carboxylic acid, mp 283°–284° C., dec

EXAMPLE 3q

7-[[(1,1'-Biphenyl)-4-ylcarbonyl]amino]-4,9-dihydro-4-methyl-9-oxopyrazolo[5,1-b]quinazoline-2-carboxylic acid, mp 278°–280° C., dec

EXAMPLE 3r 4,9-Dihydro-4-methyl-7-[(2-methylbenzoyl)amino]-9-oxopyrazolo[5,1-b]quinazoline-2-carboxylic acid, mp 274°–276° C.; dec

EXAMPLE 3s 4,9-Dihydro-7-[(4-fluorobenzoyl)amino]-4-methyl-9-oxopyrazolo[5,1-b]quinazoline-2-carboxylic acid, mp 302°–304° C., dec

EXAMPLE 3t

7-[(4-Carboxybenzoyl) aminol-4,9-dihydro-4-methyl-9-oxopyrazolo[5,1-b]quinazoline-2-carboxylic acid., mp >320° C.

EXAMPLE 3u 4,9-Dihydro-7-[(3-iodo-4-methylbenzoyl)amino]-4-methyl-9-oxopyrazolo[5,1-b]quinazoline-2-carboxylic acid, mp 322°–323° C., dec

EXAMPLE 3v

7-[(Carboxyacetyl)amino]-4,9-dihydro-4-methyl-9-oxopyrazolo[5,1-b]quinazoline-2-carboxylic acid, mp 301°–304° C., dec

EXAMPLE 3w

7-[(3-Carboxy-1-oxopropyl)amino]-4,9-dihydro-4-methyl-9-oxopyrazolo[5,1-b]qruinazoline-2-carboxylic acid, mp 274°–276° C., dec

EXAMPLE 3x

7-[(4-Carboxy-1-oxobutyl)amino]-4,9-dihydro-4-methyl-9-oxopyrazolo[5,1-b]quinazoline-2-carboxylic acid, mp 282°–284° C., dec

EXAMPLE 4

7-[Benzoyl(methyl)amino]-4,9-dihydro-4-methyl-9-oxopyrazolo[5,1-b]quinazoline-2-carboxylic acid To a stirring suspension of sodium hydride (0.05 9, 1.25 mmol, 60% dispersion in mineral oil) in 20 mL of DMF was added dropwise a solution of 7-(benzoylamino)-4,9-dihydro-4-methyl-9-oxopyrazolo-[5,1-b]quinazoline-2-carboxylic acid, ethyl ester (0.40 g, 1.02 mmol, Example 2) in 30 mL of DMF. The mixture was stirred for 30 minutes at 0° C. followed by dropwise addition of iodomethane (0.07 mL, 1.12 mmol). The ice-bath was removed, the mixture was stirred at room temperature for 2 hours, then concentrated to a yellow solid. The solid was dissolved into water, acidified to a pH of about 7 with a saturated solution of potassium phosphate, monobasic, and extracted into chloroform (2×50 mL). The combined chloroform extract was dried (MgSO₄), filtered, and concentrated. Medium pressure chromatography (silica gel, 2.5% methanol in chloroform) of the crude afforded 0.22 g (52%) of the title compound as its ethyl ester; yellow solid, mp 214°-217° C.

A suspension of the above ethyl ester in THF:water (~1:1) containing 2.5 equivalents of sodium carbonate was refluxed under N₂ for 2 hours, then allowed to cool to room temperature. The cloudy solution was filtered through a pad of Celite, the filtrate was acidified with 1N hydrochloric acid to a pH of about 3 and upon cooling a yellow solid formed. The mixture was filtered, the solid was washed with water, and vacuum-dried giving the title compound as a yellow solid, mp 268°-269° C., dec.

EXAMPLE 5

7-(Benzoyl)amino]-4,9-dihydro-4-methyl-9-oxo-N-(1H-tetrazol-5-Vl)pyrazolo [5,1-b]quinazoline-2-carboxamide A mixture of 7-(benzoylamino)-4,9-dihydro-4-methyl-9-oxopyrazolo[5,1-b]quinazoline-2-carboxylic acid (1.50 g, 4.14 mmol, Example 3) and 1,1'-carbonyldiimidazole (1.34 g, 8.26 mmol) in 100 mL of DMF is heated at 85° C. under N₂ for 30 minutes. The mixture is cooled, 5-aminotetrazole, monohydrate (0.43 g, 4.17 mmol) is added, and the resulting mixture is heated at 85° C. for 2 hours. Evaporation of the solvent gives the title compound.

EXAMPLE 6

7-(Benzoylamino)-4,9-dihydro-4-methyl-9-oxo-2-(1-H-tetrazol-5-yl) pyrazolo[5,1-b]quinazoline A mixture of 7-(benzoylamino)-4,9-dihydro-4-methyl-9-oxopyrazolo[5,1-b]quinazoline-2-carboxylic acid (1.50 g, 4.14 mmol, Example 3) in 50 mL of thionyl chloride is refluxed for 3 hours. The mixture is concentrated, the residue is cooled, and treated with cold concentrated ammonium hydroxide solution (50 mL) giving 7-(benzoylamino)-4,9-dihydro-4-methyl-9-oxopyrazolo[5,1-b]quinazoline-2-carboxamide.

A mixture of the above carboxamide (1.50 g, 4.15 mmol) in 50 mL of phosphorus oxychloride is refluxed for 2 hours, then stirred at room temperature for 48 hours. The mixture is concentrated, the residue is cooled, and suspended in 100 mL of saturated sodium bicarbonate giving 7-(benzoylamino)-4,9-dihydro-4-methyl-9-oxopyrazolo[5,1-b]quinazoline-2-carbonitrile.

To a warm solution of the above carbonitrile (1.50 g, 4.37 mmol) in 100 mL of DMF is added sodium azide (0.85 g, 13.08 mmol) and ammonium chloride (0.70 g, 13.09 mmol). The mixture is heated at 100° C. under N₂ for 24 hours, cooled, concentrated to about 35 mL, and poured into an ice-water mixture. The mixture is acidified to a pH of about 1 with 10% hydrochloric acid, and the crude product is filtered. This solid is suspended into 0.5N sodium hydroxide solution (250 mL), stirred for 1 hour at room temperature, and filtered through a pad of Celite. The filtrate is cooled, acidified with 10% hydrochloric acid to a pH of about 4 giving the title compound.

EXAMPLE 7

4,9-Dihydro-4-methyl-9-oxo-7-[(methylbenzoyl)amino]-pyrazolo[5,1-b]quinazoline-2-carboxylic acid; triethanolamine salt (1:1)

The compound of Example 3b (100 mg) is dissolved in 5 mL of triethanolamine. The mixture is diluted with ether (50 mL) and the precipitated salt is filtered, washed with ether, and air-dried to give the title compound, mp 218°-220° C.

Having described the invention, the embodiments of the invention in which an exclusive property or privilege is claimed are defined as follows:

1. The compound having the name 4,9-dihydro-4-methyl-9-oxo-7-[(4-methoxybenzoyl)-amino]-pyrazolo[5,1b]quinazoline-2-carboxylic acid.

2. The compound having the name 7-[(4-chlorobenzoyl)amino]-4,9-dihydro-4-methyl-9-oxopyrazolo[5,1-b]quinazoline-2-carboxylic acid.

3. The compound having the name 4,9-dihydro-4-methyl-9-oxo-7-[(phenylacetyl)amino]pyrazolo[5,1-b]quinazoline-2-carboxylic acid.

4. The compound having the name 7-[(3,4-dichlorobenzoyl)amino]-4,9-dihydro-4-methyl-9-oxopyrazolo[5,1-b]quinazoline-2-carboxylic acid.

5. The compound having the name 4,9-dihydro-4-methyl-9-oxo-7-[(phenylamino)carbonyl]amino]-pyrazolo[5,1-b]quinazoline-2-carboxylic acid.

6. The compound having the name 4,9-dihydro-4-methyl-9-oxo-7-[(1-oxo-3-phenyl-propyl) amino]-pyrazolo[5,1-b]quinazoline-2-carboxylic acid.

7. The compound having the name 4,9-dihydro-4-methyl-7-[(2-naphthalenylcarbonyl)amino]-9-oxopyrazolo[5,1-b]quinazoline-2-carboxylic acid.

8. The compound having the name 4,9-dihydro-7-[(4-iodobenzoyl)amino]-4-methyl-9-oxopyrazolo[5,1-b]quinazoline-2-carboxylic acid.

9. The compound having the name 4,9-dihydro-4-methyl-7-((4-nitrobenzoyl)amino]9-oxopyrazolo[5,1-b]quinazoline-2-carboxylic acid.

10. The compound having the name 4,9-dihydro-4-methyl-9-oxo-7-[(tricyclo-(3.3.1.13,7)dec-1-ylcarbonyl)amino]pyrazolo[5,1-b]quinazoline-2-carboxylic acid.

11. The compound having the name 4,9-di-hydro-4-methyl-9-oxo-7-[[(4-trifluoromethyl)benzoyl]amino]-pyrazolo[5,1-b]quinazoline-2-carboxylic acid.

12. The compound having the name 7-[([1,1'-biphenyl]-4-ylcarbonyl) amino]-4,9-dihydro-4-methyl-9-oxopyrazolo[5,1-b]quinazoline-2-carboxylic acid.

13. The compound having the name 4,9-dihydro-7-[(4-fluorobenzoyl)amino]-4-methyl-9-oxopyrazolo[5,1-b]quinazoline-2-carboxylic acid.

14. The compound having the name 7-[(4-carboxybenzoyl)amino]-4,9-dihydro-4-methyl-9-oxopyrazolo[5,1-b]quinazoline-2-carboxylic acid.

15. The compound having the name 4,9-dihydro-7-[(3-iodo-4-methylbenzoyl)amino]-4-methyl-9-oxopyrazolo[5,1-b]quinazoline-2-carboxylic acid.

16. The compound having the name 7-[(carboxyacetyl)amino]-4,9-dihydro-4-methyl-9-oxopyrazolo[5,1-b]quinazoline-2-carboxylic acid.

17. The compound having the name 7-[(3-carboxy-1-oxopropyl)amino]-4,9-dihydro-4-methyl-9-oxopyrazolo[5,1-b]quinazoline-2-carboxylic acid.

18. The compound of claim 1 having the name 7-[(4-carboxy-1-oxobutyl)amino]-4,9-dihydro-4-methyl-9-oxopyrazolo[5,1-b]quinazoline-2-carboxylic acid.

* * * * *

UNITED STATES PATENT AND TRADEMARK OFFICE
CERTIFICATE OF CORRECTION

PATENT NO. : 5,342,942
DATED : August 30, 1994
INVENTOR(S) : Juan C. Jaen et al.

It is certified that error appears in the above-indentified patent and that said Letters Patent is hereby corrected as shown below:

On column 2, line 47, please delete "NFG" and substitute therefore --NGF--

On column 6, line 65, please delete "—NH$_2$" and substitute therefore --7-NH$_2$--

On column 11, line 24, please delete "COOEr)." and substitute therefore --COOEt).--

On column 11, line 52, please delete "hydrolyric" and substitute therefore --hydrolytic--

On column 18, line 55, please delete "9," and substitute therefore --g,--

On column 19, line 21, please delete "5-Vl " and substitute therefore --5-yl)--

On column 20, line 42 (claim 10), please delete "(3.3.1.13,7)" and substitute therefore --(3.3.1.1$^{3,7}$)--

On column 20, line 44 (claim 11), please delete "di-hydro" and substitute therefore --dihydro--

UNITED STATES PATENT AND TRADEMARK OFFICE
CERTIFICATE OF CORRECTION

PATENT NO. : 5,342,942

DATED : August 30, 1994

INVENTOR(S) : Juan C. Jaen et al

It is certified that error appears in the above-indentified patent and that said Letters Patent is hereby corrected as shown below:

On column 20, line 65 (claim 18), please delete "of claim 1" after the word "compound"

Signed and Sealed this

Twenty-seventh Day of December, 1994

Attest:

BRUCE LEHMAN

Attesting Officer

Commissioner of Patents and Trademarks